United States Patent
Damm et al.

(10) Patent No.: US 7,896,913 B2
(45) Date of Patent: Mar. 1, 2011

(54) ANCHORING SYSTEM FOR IMPLANTABLE HEART VALVE PROSTHESES

(75) Inventors: Christoph Damm, Jena (DE); Carsten Weber, Jena (DE); Stefan Risse, Jena (DE); Volker Guyenot, Jena (DE); Matthias Mohaupt, Altengonna (DE); Gerd Harnisch, Jena (DE); Peggy Dorrer, Gottingen (DE); Markus Ferrari, Jena (DE); Klaus Lang, Cospeda (DE); Hans-Reiner Figulla, Jena (DE)

(73) Assignee: JenaValve Technology, Inc., Wilmington, DE (US)

( * ) Notice: Subject to any disclaimer, the term of this patent is extended or adjusted under 35 U.S.C. 154(b) by 0 days.

(21) Appl. No.: 11/515,589

(22) Filed: Sep. 5, 2006

(65) Prior Publication Data
US 2007/0005129 A1    Jan. 4, 2007

Related U.S. Application Data

(63) Continuation of application No. 10/204,918, filed as application No. PCT/DE01/00836 on Feb. 28, 2001, now abandoned.

(30) Foreign Application Priority Data

Feb. 28, 2000   (DE) ............................... 100 10 073

(51) Int. Cl.
*A61F 2/06*     (2006.01)
*A61F 2/24*     (2006.01)
(52) U.S. Cl. ..................... 623/1.36; 623/2.23; 623/2.38

(58) Field of Classification Search ................ 623/1.14, 623/1.36, 2.11, 2.14, 2.17, 2.18, 2.23, 2.38, 623/2.39, 2.4, 900
See application file for complete search history.

(56) References Cited

U.S. PATENT DOCUMENTS

| 4,214,587 A | 7/1980 | Sakura, Jr. |
| 4,485,816 A | 12/1984 | Krumme |
| 4,687,483 A | 8/1987 | Fisher et al. |

(Continued)

FOREIGN PATENT DOCUMENTS

DE    195 46 692 A1    6/1997

(Continued)

OTHER PUBLICATIONS

Aortenklappenbioprothese erfolgreich in der Entwicklung, (1 page) May 16, 2003.

(Continued)

*Primary Examiner*—David H Willse
*Assistant Examiner*—Javier G Blanco
(74) *Attorney, Agent, or Firm*—Finnegan, Henderson, Farabow, Garrett & Dunner, L.L.P.

(57) ABSTRACT

The invention relates to an anchoring system for heart valve prostheses which can be implanted by introduction via the aorta without any major surgical operation. With the heart valve prosthesis according to the invention it shall be achieved that this can be safely and quickly guided through the aorta toward the heart, and can be fixed there. With this, hook-shaped elements are secured to the commissures of the heart valve prosthesis the hooks of which are guided in an outward direction through the heart valve prosthesis material.

19 Claims, 4 Drawing Sheets

U.S. PATENT DOCUMENTS

| | | |
|---|---|---|
| 5,002,566 A | 3/1991 | Carpentier et al. |
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,207,695 A * | 5/1993 | Trout, III .................... 623/1.36 |
| 5,234,447 A | 8/1993 | Kaster et al. |
| 5,279,612 A | 1/1994 | Eberhardt |
| 5,330,500 A | 7/1994 | Song |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,370,685 A | 12/1994 | Stevens |
| 5,411,552 A | 5/1995 | Andersen et al. |
| 5,456,713 A | 10/1995 | Chuter |
| 5,489,298 A | 2/1996 | Love et al. |
| 5,509,930 A | 4/1996 | Love |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,817,113 A * | 10/1998 | Gifford et al. ................ 606/153 |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,855,601 A * | 1/1999 | Bessler et al. .............. 623/2.38 |
| 5,876,434 A | 3/1999 | Flomenblit et al. |
| 5,880,242 A | 3/1999 | Hu et al. |
| 5,891,160 A | 4/1999 | Williamson, IV et al. |
| 5,899,936 A | 5/1999 | Goldstein |
| 5,928,281 A | 7/1999 | Huynh et al. |
| 5,935,163 A | 8/1999 | Gabbay |
| 5,104,407 A | 9/1999 | Lam et al. |
| 5,984,959 A | 11/1999 | Robertson et al. |
| 6,001,126 A | 12/1999 | Nguyen-Thien-Nhon |
| 5,061,277 A | 2/2000 | Carpentier et al. |
| 6,074,416 A | 6/2000 | Berg et al. |
| 6,077,297 A | 6/2000 | Robinson et al. |
| 6,093,530 A | 7/2000 | McIlroy et al. |
| 6,102,944 A | 8/2000 | Huynh et al. |
| 6,106,550 A | 8/2000 | Magovern et al. |
| 6,113,612 A * | 9/2000 | Swanson et al. ........... 623/1.15 |
| 6,117,169 A | 9/2000 | Moe |
| 6,126,685 A | 10/2000 | Lenker et al. |
| 6,152,937 A | 11/2000 | Peterson et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,283,995 B1 | 9/2001 | Moe et al. |
| 6,287,338 B1 | 9/2001 | Sarnowski et al. |
| 6,334,873 B1 | 1/2002 | Lane et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,511,491 B2 | 1/2003 | Grudem et al. |
| 6,517,573 B1 | 2/2003 | Pollock et al. |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,589,279 B1 | 7/2003 | Anderson et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,037,333 B2 | 5/2006 | Myers et al. |
| 7,078,163 B2 | 7/2006 | Torrianni |
| 7,081,132 B2 | 7/2006 | Cook et al. |
| 7,137,184 B2 | 11/2006 | Schreck et al. |
| 7,141,064 B2 | 11/2006 | Scott et al. |
| 7,147,662 B1 | 12/2006 | Pollock et al. |
| 7,147,663 B1 | 12/2006 | Berg et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,381,218 B2 | 6/2008 | Schreck |
| 7,393,360 B2 | 7/2008 | Spenser et al. |
| 2001/0011187 A1 | 8/2001 | Pavcnik et al. |
| 2001/0039450 A1 | 11/2001 | Pavcnik et al. |
| 2002/0032481 A1 | 3/2002 | Gabbay |
| 2002/0055775 A1 | 5/2002 | Carpentier et al. |
| 2002/0123790 A1 | 9/2002 | White et al. |
| 2002/0133226 A1 | 9/2002 | Marquez et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |

| | | | |
|---|---|---|---|
| 2003/0195620 A1 | 10/2003 | Huynh et al. | |
| 2003/0236570 A1 | 12/2003 | Cook et al. | |
| 2004/0006380 A1 | 1/2004 | Buck et al. | |
| 2004/0039436 A1 | 2/2004 | Spenser et al. | |
| 2004/0049262 A1 | 3/2004 | Obermiller et al. | |
| 2004/0073289 A1 | 4/2004 | Hartley et al. | |
| 2004/0078950 A1 | 4/2004 | Schreck et al. | |
| 2004/0117004 A1 | 6/2004 | Osborne et al. | |
| 2004/0117009 A1 | 6/2004 | Cali et al. | |
| 2004/0148018 A1 | 7/2004 | Carpentier et al. | |
| 2004/0153145 A1 | 8/2004 | Simionescu et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0193244 A1 | 9/2004 | Hartley et al. | |
| 2004/0210301 A1 | 10/2004 | Obermiller et al. | |
| 2004/0260389 A1 | 12/2004 | Case et al. | |
| 2005/0009000 A1 | 1/2005 | Wilhelm et al. | |
| 2005/0033220 A1 | 2/2005 | Wilk et al. | |
| 2005/0043790 A1 | 2/2005 | Seguin | |
| 2005/0049692 A1 | 3/2005 | Numamoto et al. | |
| 2005/0075725 A1 | 4/2005 | Rowe | |
| 2005/0075776 A1 | 4/2005 | Cho | |
| 2005/0096726 A1 | 5/2005 | Sequin et al. | |
| 2005/0096736 A1 | 5/2005 | Osse et al. | |
| 2005/0098547 A1 | 5/2005 | Cali et al. | |
| 2005/0113910 A1 | 5/2005 | Paniagua et al. | |
| 2005/0119728 A1 | 6/2005 | Sarac | |
| 2005/0119736 A1 | 6/2005 | Zilla et al. | |
| 2005/0137687 A1 | 6/2005 | Salahieh et al. | |
| 2005/0137688 A1 | 6/2005 | Salahieh et al. | |
| 2005/0137690 A1 | 6/2005 | Salahieh et al. | |
| 2005/0137697 A1 | 6/2005 | Salahieh et al. | |
| 2005/0137698 A1 | 6/2005 | Salahieh et al. | |
| 2005/0137702 A1 | 6/2005 | Haug et al. | |
| 2005/0143804 A1 | 6/2005 | Haverkost | |
| 2005/0143807 A1 | 6/2005 | Pavcnik et al. | |
| 2005/0149166 A1 | 7/2005 | Schaeffer et al. | |
| 2005/0150775 A1 | 7/2005 | Zhang et al. | |
| 2005/0171597 A1 | 8/2005 | Boatman et al. | |
| 2005/0171598 A1 | 8/2005 | Schaeffer | |
| 2005/0192665 A1 | 9/2005 | Spenser et al. | |
| 2005/0197695 A1 | 9/2005 | Stacchino et al. | |
| 2005/0222668 A1 | 10/2005 | Schaeffer et al. | |
| 2005/0234546 A1 | 10/2005 | Nugent et al. | |
| 2005/0267560 A1 | 12/2005 | Bates | |
| 2006/0009842 A1 | 1/2006 | Huynh et al. | |
| 2006/0025857 A1 | 2/2006 | Bergheim et al. | |
| 2006/0047343 A1 | 3/2006 | Oviatt et al. | |
| 2006/0058864 A1 | 3/2006 | Schaeffer et al. | |
| 2006/0074484 A1 | 4/2006 | Huber | |
| 2006/0111770 A1 | 5/2006 | Pavcnik et al. | |
| 2006/0142846 A1 | 6/2006 | Pavcnik et al. | |
| 2006/0149360 A1 | 7/2006 | Schwammenthal et al. | |
| 2006/0167543 A1 | 7/2006 | Bailey et al. | |
| 2006/0193885 A1 | 8/2006 | Neethling et al. | |
| 2006/0210597 A1 | 9/2006 | Hiles | |
| 2006/0229718 A1 | 10/2006 | Marquez | |
| 2006/0229719 A1 | 10/2006 | Marquez et al. | |
| 2006/0246584 A1 | 11/2006 | Covelli | |
| 2006/0259134 A1 | 11/2006 | Schwammenthal et al. | |
| 2006/0259136 A1 | 11/2006 | Nguyen et al. | |
| 2006/0265056 A1 | 11/2006 | Nguyen et al. | |
| 2006/0287717 A1 | 12/2006 | Rowe et al. | |
| 2006/0287719 A1 | 12/2006 | Rowe et al. | |
| 2006/0290027 A1 | 12/2006 | O'Connor et al. | |
| 2006/0293745 A1 | 12/2006 | Carpentier et al. | |
| 2007/0005129 A1 | 1/2007 | Damm et al. | |
| 2007/0005131 A1 | 1/2007 | Taylor | |
| 2007/0005132 A1 | 1/2007 | Simionescu et al. | |
| 2007/0020248 A1 | 1/2007 | Everaerts et al. | |
| 2007/0021826 A1 | 1/2007 | Case et al. | |
| 2007/0038291 A1 | 2/2007 | Case et al. | |
| 2007/0038295 A1 | 2/2007 | Case et al. | |
| 2007/0050014 A1 | 3/2007 | Johnson | |
| 2007/0088431 A1 | 4/2007 | Bourang et al. | |
| 2007/0093887 A1 | 4/2007 | Case et al. | |
| 2007/0100435 A1 | 5/2007 | Case et al. | |
| 2007/0100440 A1 | 5/2007 | Figulla et al. | |
| 2007/0112422 A1 | 5/2007 | Dehdashtian | |
| 2007/0123700 A1 | 5/2007 | Ueda et al. | |
| 2007/0123979 A1 | 5/2007 | Perier et al. | |
| 2007/0142906 A1 | 6/2007 | Figulla et al. | |
| 2007/0162103 A1 | 7/2007 | Case et al. | |
| 2007/0173932 A1 | 7/2007 | Cali et al. | |
| 2007/0179592 A1 | 8/2007 | Schaeffer | |
| 2007/0185565 A1 | 8/2007 | Schwammenthal et al. | |
| 2007/0203576 A1 | 8/2007 | Lee et al. | |
| 2007/0213813 A1 | 9/2007 | Von Segesser et al. | |
| 2007/0244551 A1 | 10/2007 | Stobie | |
| 2007/0260327 A1 | 11/2007 | Case et al. | |
| 2007/0288087 A1 | 12/2007 | Fearnot et al. | |
| 2008/0004688 A1 | 1/2008 | Spenser et al. | |
| 2008/0021546 A1 | 1/2008 | Patz et al. | |
| 2008/0033534 A1 | 2/2008 | Cook et al. | |
| 2008/0065011 A1 | 3/2008 | Marchand et al. | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. | |
| 2008/0071369 A1 | 3/2008 | Tuval et al. | |
| 2008/0086205 A1 | 4/2008 | Gordy et al. | |
| 2008/0097586 A1 | 4/2008 | Pavcnik et al. | |
| 2008/0102439 A1 | 5/2008 | Tian et al. | |
| 2008/0262602 A1 | 10/2008 | Wilk et al. | |

FOREIGN PATENT DOCUMENTS

| | | | |
|---|---|---|---|
| DE | 19546692 A1 | 6/1997 | |
| DE | 20003874 U1 | 6/2000 | |
| DE | 198 57 887 A1 | 7/2000 | |
| DE | 19857887 A1 | 7/2000 | |
| DE | 10010073 A1 | 9/2001 | |
| DE | 10010074 A1 | 10/2001 | |
| DE | 101 21 210 A1 | 11/2002 | |
| DE | 19546692 C2 | 11/2002 | |
| DE | 10010074 B4 | 4/2005 | |
| DE | 19857887 B4 | 5/2005 | |
| DE | 10010073 B4 | 12/2005 | |
| EP | 0084395 A1 | 7/1983 | |
| EP | 0458877 | 8/1990 | |
| EP | 0402036 B1 | 12/1990 | |
| EP | 0402176 B1 | 12/1990 | |
| EP | 0458877 B1 | 4/1991 | |
| EP | 0515324 A1 | 11/1992 | |
| EP | 0547135 B1 | 6/1993 | |
| EP | 0871414 | 9/1995 | |
| EP | 0 592 410 B1 | 10/1995 | |
| EP | 0756498 | 10/1995 | |
| EP | 0786970 | 5/1996 | |
| EP | 0729364 B1 | 9/1996 | |
| EP | 0756498 B1 | 5/1997 | |
| EP | 0778775 B1 | 6/1997 | |
| EP | 0786970 | 8/1997 | |
| EP | 0888142 | 9/1997 | |
| EP | 0971649 | 10/1998 | |
| EP | 0 896 813 A2 | 2/1999 | |
| EP | 0928615 A1 | 7/1999 | |
| EP | 1051204 | 7/1999 | |
| EP | 1089676 | 12/1999 | |
| EP | 0986348 B1 | 3/2000 | |
| EP | 1117446 | 4/2000 | |
| EP | 1 164 976 | 8/2000 | |
| EP | 1158937 | 9/2000 | |
| EP | 1041942 B1 | 10/2000 | |

| | | |
|---|---|---|
| EP | 1041943 B1 | 10/2000 |
| EP | 1171061 | 10/2000 |
| EP | 1206179 | 2/2001 |
| EP | 1117446 B1 | 7/2001 |
| EP | 1 255 510 | 8/2001 |
| EP | 1259193 | 9/2001 |
| EP | 1206179 B1 | 5/2002 |
| EP | 1347785 | 8/2002 |
| EP | 1235537 | 9/2002 |
| EP | 1248655 | 10/2002 |
| EP | 1251804 B1 | 10/2002 |
| EP | 1257305 | 11/2002 |
| EP | 0 971 649 B1 | 12/2002 |
| EP | 1395208 | 12/2002 |
| EP | 1 401 359 | 1/2003 |
| EP | 1406561 | 1/2003 |
| EP | 1281357 A2 | 2/2003 |
| EP | 1408882 | 2/2003 |
| EP | 1 435 878 | 4/2003 |
| EP | 1 435 879 | 4/2003 |
| EP | 1 441 672 | 6/2003 |
| EP | 1 017 868 B1 | 9/2003 |
| EP | 1354569 A1 | 10/2003 |
| EP | 1494616 | 10/2003 |
| EP | 1 519 697 | 1/2004 |
| EP | 1 539 047 | 4/2004 |
| EP | 1551274 | 4/2004 |
| EP | 1 560 542 | 5/2004 |
| EP | 1414295 | 5/2004 |
| EP | 1 603 493 | 9/2004 |
| EP | 1452153 A1 | 9/2004 |
| EP | 0987998 B1 | 10/2004 |
| EP | 1499366 B1 | 1/2005 |
| EP | 1 663 070 | 3/2005 |
| EP | 1 253 875 B1 | 4/2005 |
| EP | 1 667 614 | 4/2005 |
| EP | 1 251 803 B1 | 6/2005 |
| EP | 1 702 247 | 7/2005 |
| EP | 1734902 | 8/2005 |
| EP | 1835948 | 6/2006 |
| EP | 1863545 | 9/2006 |
| EP | 1893132 | 11/2006 |
| EP | 1901681 | 12/2006 |
| EP | 1835948 | 9/2007 |
| EP | 1112042 B1 | 11/2007 |
| EP | 1878407 A1 | 1/2008 |
| EP | 1886649 A2 | 2/2008 |
| EP | 1259195 B1 | 10/2008 |
| EP | 1994913 | 11/2008 |
| GB | 2440809 A | 2/2008 |
| JP | 2002-525169 | 8/2002 |
| JP | 2002-536115 | 10/2002 |
| JP | 2003-523262 | 8/2003 |
| JP | 2003-524504 | 8/2003 |
| JP | 2005-118585 | 5/2005 |
| JP | 2007-296375 | 11/2007 |
| WO | WO-90/09102 | 8/1990 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO 98/43556 | 10/1998 |
| WO | WO-98/46165 | 10/1998 |
| WO | WO 9915112 A1 * | 4/1999 |
| WO | WO-99/37337 | 7/1999 |
| WO | WO-99/66863 | 12/1999 |
| WO | WO 00/15148 | 3/2000 |
| WO | WO 00/18333 | 4/2000 |
| WO | WO-00/18445 | 4/2000 |
| WO | WO 00/47139 A1 | 8/2000 |
| WO | WO 0044311 | 8/2000 |
| WO | WO-00/53125 | 9/2000 |
| WO | WO-00/62714 | 10/2000 |
| WO | WO-01/10209 A1 | 2/2001 |
| WO | WO-01/41679 A1 | 6/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/013239 | 2/2003 |
| WO | WO 03/028592 A1 | 4/2003 |
| WO | WO 03/047468 A1 | 6/2003 |
| WO | WO 00/047139 | 8/2003 |
| WO | WO-03/079928 A2 | 10/2003 |
| WO | WO 2004/004597 A2 | 1/2004 |
| WO | WO 2004/019825 A1 | 3/2004 |
| WO | WO-2004/026117 A2 | 4/2004 |
| WO | WO 2004/043301 A1 | 5/2004 |
| WO | WO 2004/082527 A2 | 9/2004 |
| WO | WO 2005/021063 A2 | 3/2005 |
| WO | WO 2005/034812 A1 | 4/2005 |
| WO | WO 2005/062980 A | 7/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A1 | 6/2006 |
| WO | WO 2006/076890 A1 | 7/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/127756 A2 | 11/2006 |
| WO | WO-2006/132948 A1 | 12/2006 |
| WO | WO-2007/071436 A2 | 6/2007 |
| WO | WO-2008/028569 A1 | 3/2008 |
| WO | WO 2008/045949 | 4/2008 |

OTHER PUBLICATIONS

Translation of Aortenklappenbioprothese erfolgreich in der Entwicklung (2 pages).

Screen shots from http://www.fraunhofer.de/presse/filme/2006/index.jsp (2 pages), 2006.

Liang, Ma, et al., "Double-crowned valved stents for off-pump mitral valve replacement," European Journal of Cardio-Thoracic Surgery, 194-198 (5 pages), Jun. 13, 2005.

Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.

Translation of DE 19546692 A1 (4 pages).

Translation of EP 1469797 B1 (16 pages).

File history for German Patent DE 195 46 692 filed Dec. 14, 1995 and patented Jul. 11, 2002.

* cited by examiner

ANCHORING SYSTEM FOR IMPLANTABLE HEART VALVE PROSTHESES

CROSS REFERENCE TO RELATED APPLICATIONS

This application is a continuation of U.S. Ser. No. 10/204,918 filed Nov. 27, 2002, now abandoned. U.S. Ser. No. 10/204,918 is the U.S. national phase of PCT/DE01/00836 filed Feb. 28, 2001. PCT/DE01/00836 claims priority to German patent application 100 10 073.2 filed Feb. 28, 2000. The disclosures of all of these applications are hereby incorporated herein by reference.

The invention relates to an anchoring system for heart valve prostheses which is implantable via the aorta by introduction without any major surgical operation wherein in conventional manner complete opening of the thorax has been required.

In the past the most different attempts have been made and solutions have been offered as well wherein heart valve prostheses should be guided through the aorta towards the heart, and be fixedly implanted there after a deploying and stretching over operation.

Thus, in U.S. Pat. No. 5,855,601, among other things, a so-called stent is described to which a heart valve prosthesis can be secured. This stent is essentially formed of a wire-shaped form storage metal which represents a cylindrical structure within a grid structure. The form storage metal can be folded at temperatures below 37° C., and shall be guided by means of a catheter via the aorta towards the heart, and there it shall take up the memorized shape after a cooling system has been switched off and a temperature of about 37° C. has been achieved, and shall closely fit in the respective deployed condition on the inside aorta wall.

Due to the limitations of the form storage metal, however, it is difficult for such a stent to be miniaturized and folded up so far in order to be guided through the aorta problem-free, and also to be dimensioned in the deployed state such that then it closely fits on the inside aorta wall, and will be safely supported as well.

Moreover, manufacturing an anchoring support which is constructed and designed in such a manner and made of conventional form storage metal (for example, Nitinol) being suitable in the required temperature range is encountered with problems and requires an appropriate high manufacturing amount since as a rule such a body is cut out of solid material by laser beam cutting.

Hence, it is an object of the invention to suggest a possibility wherein heart valve prostheses are allowed to be guided via the aorta towards the heart, and be fixed there.

According to the invention this object is solved with the features of claim 1. Advantageous embodiments and improvements of the invention result from the features mentioned in the subclaims.

According to the invention, hook-shaped elements are secured immediately to the commissures of a biological heart valve prosthesis which can be removed from a pig's heart, for example, or otherwise to an artificial heart valve prosthesis, which hooks thereof are guided outside through the heart valve prosthesis material, and which in the implanted condition are stuck into the aorta wall and piercing the aorta wall, respectively such that the heart valve prosthesis can be safely secured to the aorta wall.

Further additional hook-shaped elements can also be secured to the outer ring of the heart valve prosthesis.

On that occasion, the hook-shaped elements can be sewn onto the heart valve prosthesis.

However, it is simpler and requires less amount for the hook-shaped elements to be introduced from the inside into the heart valve prosthesis, and at least for the hooks to be pushed through the heart valve prosthesis material wherein it is proper for the hook-shaped elements to be formed on a ridge or with a base element whereby it will be assured that merely the hooks of the hook-shaped elements protrude from the heart valve prosthesis, and the remaining portion having a respective size maintains the retention inside the heart valve prosthesis.

Thus, for example, a ridge can be in the form of a flat bar and an elongated plate, respectively, on which at least two hook-shaped elements are designed.

A base element, for example, can be designed in a plate-shaped manner of a circular form, wherein the cross-sectional area of the circle can prevent the heart valve prosthesis material from being pierced.

The hook-shaped elements which are arranged on ridges and base elements, respectively, are allowed to be substantially formed in a pin-shaped manner. On that occasion, one or a plurality of barbs are formed on the pin-shaped portion for anchoring in the aorta wall which interlock in or behind the aorta wall after pressing-in.

On that occasion, the barb shape can be memorized into a form storage metal such that the barbs protrude outwardly directed above the transition temperatures only, and so cutting-in and piercing the aorta wall is facilitated.

If ridges are used on which the hook-shaped elements are formed or secured to, these are allowed to be secured to the commissures of a heart valve prosthesis such that they are aligned in the longitudinal direction of the aorta in the implanted state.

However, it can also be particularly advantageous for the ridges to be designed in a helical manner such that they are adapted to the inner contour of the aorta due to the helical shape, and closely fit immediately to this by means of the hooks wherein a greater circumferential area of the inner aorta wall can be covered and an increased degree of closeness can be achieved due to the helical shape.

If individual hook-shaped elements being otherwise separated from each other are used with base elements these should also be arranged over the commissures in a distributed manner wherein a configuration following the helical shape or a configuration of two counterwound spirals is possible as well.

If ridges having hook-shaped elements are used these ridges should have a length which is at least as large as the length of the commissures of the heart valve prosthesis.

The ridges secured to the different commissures are not connected to one another.

For introducing the heart valve prosthesis with the anchoring system secured thereto it is also favorable if at least the hook-shaped elements are made of a form storage metal which maintains that the hook-shaped elements sit flat during the phase of introduction, and only low resistance of introduction and low volume are obtained and the desired shape and erecting the hooks for anchoring in the aorta wall only occur at the site of implantation.

The effective height of the hook-shaped elements then at least should be 2 mm such that they protrude from the heart valve prosthesis in this height, and penetrate into the aorta wall and pierce it, respectively.

It is also advantageous to bend the hooks of the various hook shaped elements in different directions such that a secure fixation of the anchoring system according to the invention can be achieved while taking into account the conditions inside the aorta, pressure and flow conditions in the vicinity of the heart as well.

Advantageously, the adjacent hook-shaped elements can be bent directed towards each other, and such a position can be memorized, respectively, with the use of form storage metal. That results in cramping of the adjacent hook-shaped elements inside the aorta wall with reaching and exceeding the transition temperature, respectively.

Further, inside the heart valve prosthesis in the area of the outer ring thereof an additional annular member is allowed to be secured which can also be pressed during the phase of introduction through the aorta, and which demands a smaller volume. For this, an elastomer material such as for example a suitable plastic and rubber, respectively, provided with a helical spring as the case may be or only a helical spring as well or a form storage metal can be used.

The heart valve prosthesis provided with the anchoring system according to the invention can be introduced into the aorta by means of a catheter on which a corresponding mechanism is formed wherein the mechanism should maintain deploying the heart valve prosthesis and releasing the heart valve prosthesis placed in the desired position.

It is also possible to employ a balloon catheter wherein the heart valve prosthesis provided with the anchoring system according to the invention can be put on and introduced in this position into the aorta. If the site of implantation is reached the balloon is pressurized then, and the heart valve prosthesis is pressed with the hook-shaped elements against the aorta wall, and then the hooks are allowed to be anchored inside the aorta wall wherein using the form storage metal the balloon catheter can also be used for required cooling.

The surface of the balloon of such a catheter can be appropriately contoured such that, for example, the base elements and the ridges, respectively, are safely supported in the phase of passing through the aorta due to the elasticity of the balloon and the appropriately designed contour of the ridges and base elements, respectively, and this retention can be released.

However, a catheter having a self-deploying mechanism can also be used which in turn consists of a form storage metal as well, to ensure the attachment of the heart valve prosthesis with the anchoring system according to the invention.

In each case, however, in the phase of passing through the aorta it is appropriate to envelope the heart valve prosthesis in order to avoid undesired injuries of the aorta wall before arriving at the site of implantation, and also to ensure an appropriate thermal insulation with the required cooling as well. After arriving at the site of implantation this enclosure can be torn, and an unlocking mechanism can be activated, respectively, and removed again along with the catheter from the aorta.

If a deploying mechanism made of a form storage metal is used, as already mentioned, this is allowed to be designed as an annular element which is secured to the heart valve prosthesis in the area of the outer ring thereof. Such an annular element is allowed then to ensure the stability of the implanted heart valve prosthesis, and an increased sealing function.

BRIEF DESCRIPTION OF THE DRAWINGS

In the text that follows the invention will be explained in more detail in connection with the drawings illustrating the various embodiments. In the drawings.

DETAILED DESCRIPTION OF ILLUSTRATIVE EMBODIMENTS

Figure 1:
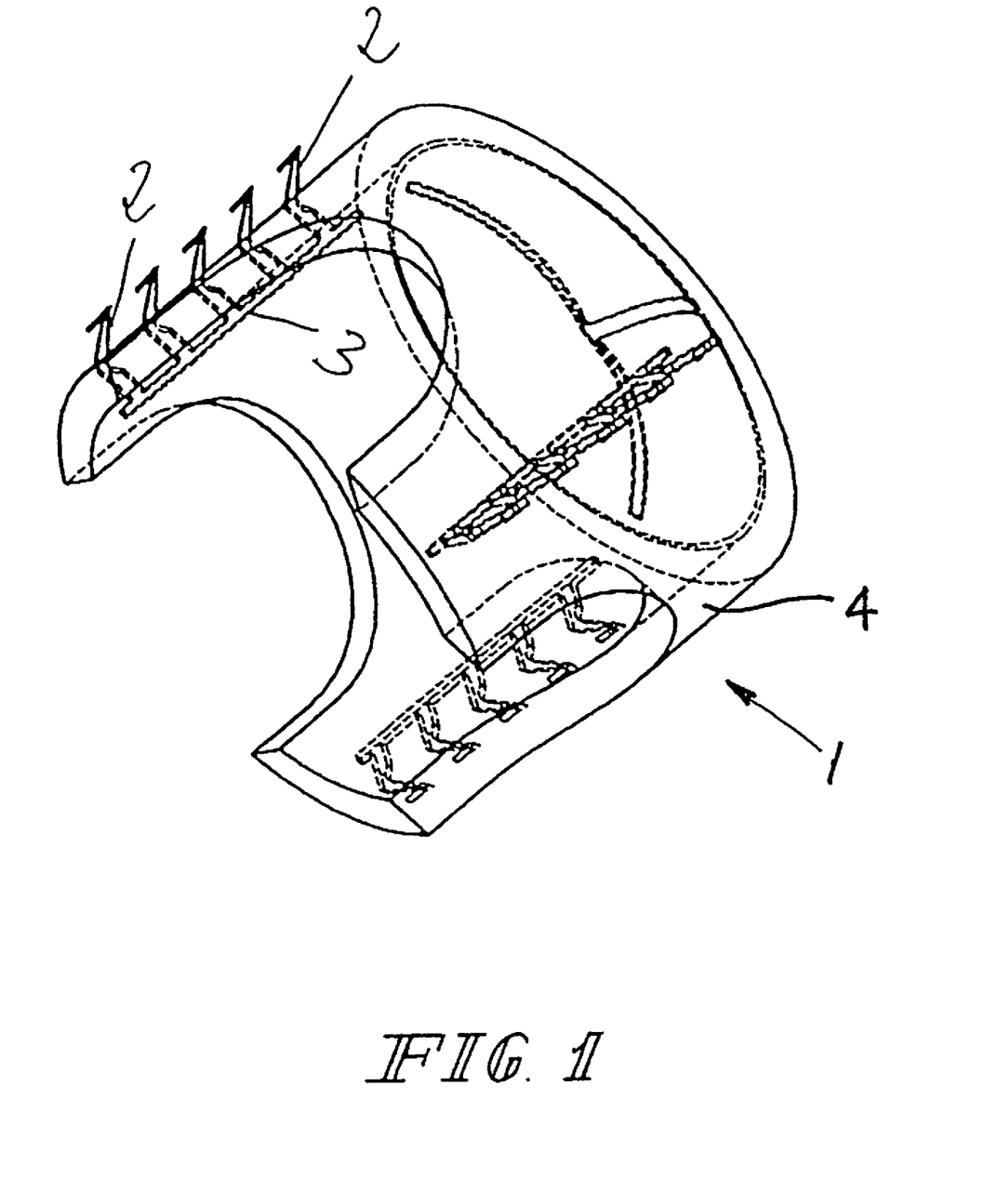
FIG. 1 illustrates an embodiment of the anchoring system according to the invention on-a heart valve prosthesis.
Figures 2, 3, 4:
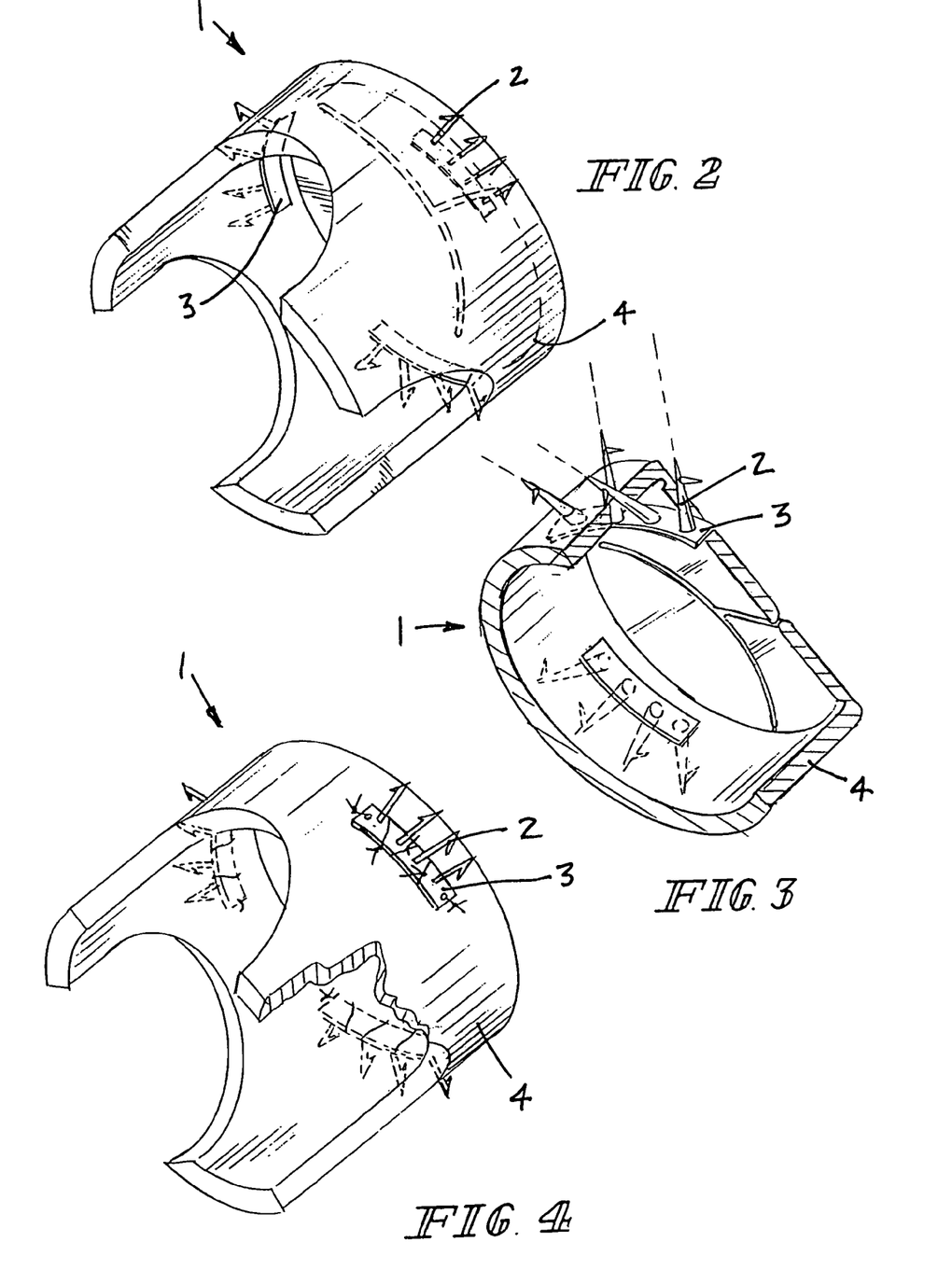
FIG. 2 illustrates a perspective view of another embodiment of the anchoring system according to the invention on a heart valve prosthesis.
FIG. 3 illustrates a sectional perspective view of another embodiment of the anchoring system according to the invention on a heart valve prosthesis.
FIG. 4 illustrates a partly broken away perspective view of another embodiment of the anchoring system according to the invention on a heart valve prosthesis.
Figure 5:
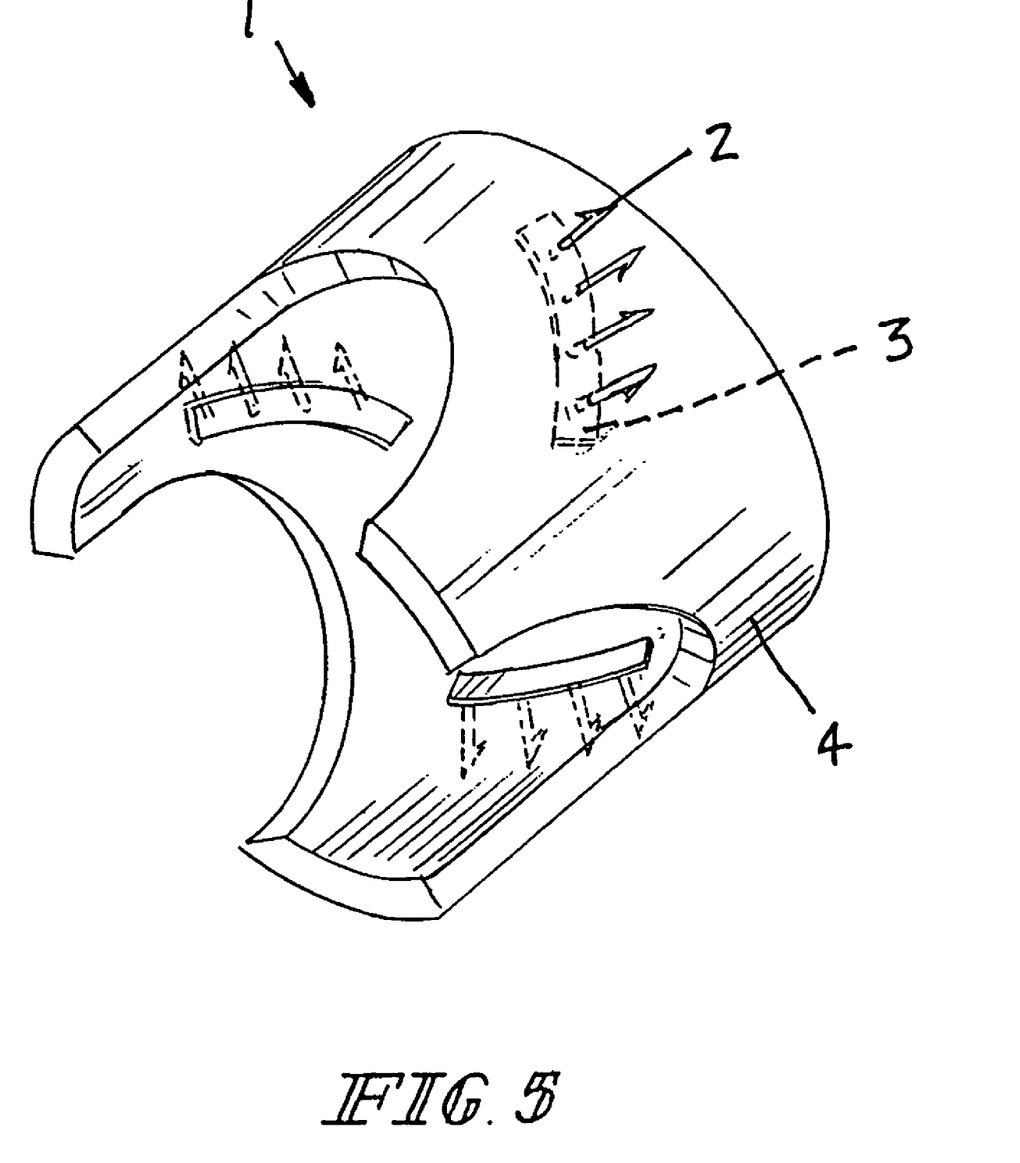
FIG. 5 illustrates a perspective view of another embodiment of the anchoring system according to the invention on a heart valve prosthesis.

With the embodiment of an anchoring system according to the invention for a heart valve prosthesis 1 as shown in FIG. 1 there are hook-shaped elements 2 formed on ridges 3, and each ridge 3 is located on a commissure of the heart valve prosthesis 1, and is secured there.

With this embodiment, both the ridges 3 and the hook-shaped elements 2 are made of a form storage metal available, for example, under the designation of Nitinol. For the attachment the ridges 3 are introduced from the inside into the heart valve prosthesis 1 and simply pressed through the commissures of the heart valve prosthesis 1 such that this will be pierced.

Figure 6:
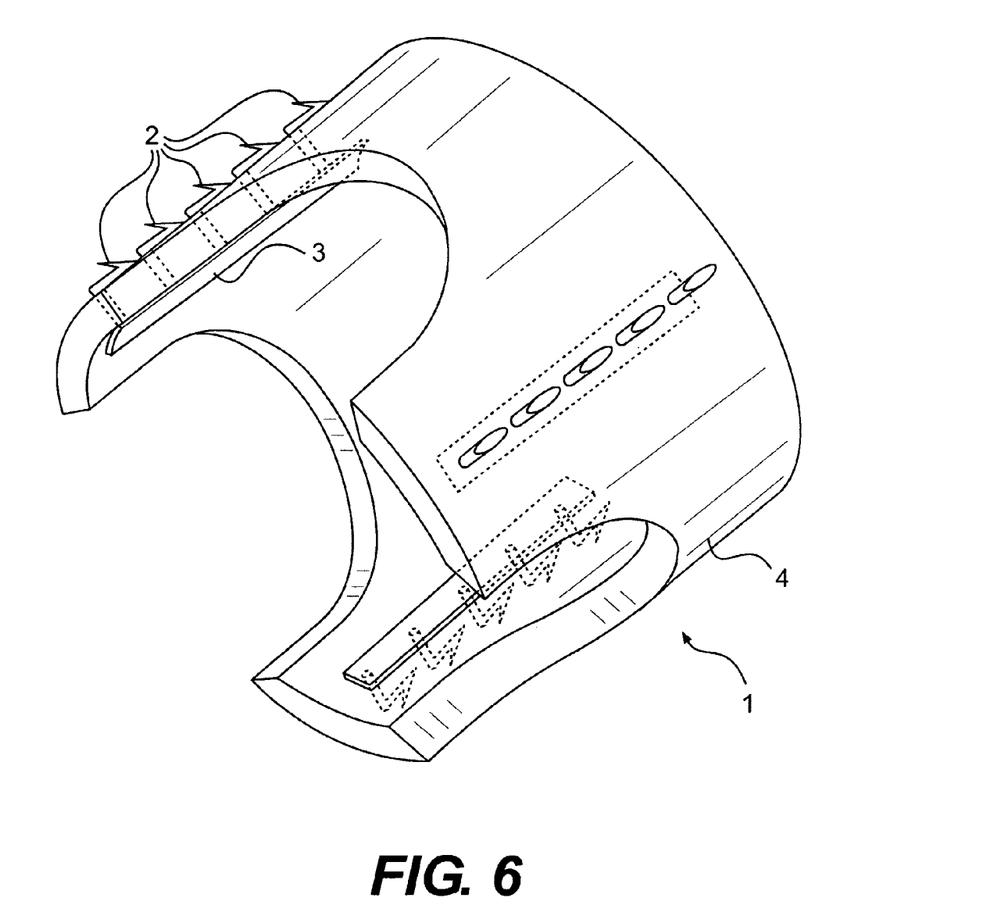
FIG. 6 illustrates a perspective view of another embodiment of the anchoring system according to the invention on a heart valve prosthesis.

The form storage metal can be memorized into the shape as shown in FIG. 1 which will be taken up after the transition temperature of 37° C. has been exceeded. In the phase of introduction of the heart valve prosthesis 1, however, the hook-shaped elements 2 should be inclined almost 90° in the direction towards the longitudinal axis of the ridges 3 as far as possible such that they require a relatively small volume and slightly protrude such that introducing is facilitated, and injuries of the aorta wall can be avoided. See FIG. 6.

With the embodiment as shown herein, five hook-shaped elements each are formed on the ridge 3. Altogether, at least fifteen hook-shaped elements should be used, however.

However, the number of the hook-shaped elements 2 can be readily varied, and moreover it is possible for a plurality of such ridges 3 having hook-shaped elements 2 to be secured to a commissure of the heart valve prosthesis 1.

On that occasion, the ridges 3 are allowed to be aligned inclined with an angle which is not shown here, wherein two such ridges 3 can also be inclined opposite to each other.

In the form which is not shown, an additional annular element can be secured to the heart valve prosthesis 1 in the area of the outer ring 4 thereof.

In addition, barbs can be formed on the hook-shaped elements 2 and the hooks thereof, respectively, to improve fastening.

What is claimed is:

1. An implantable heart valve prosthesis including a prosthetic valve component and an anchoring system, the anchoring system including a plurality of elongated discrete base elements attached to the prosthetic valve component, each having a longitudinal axis, and a plurality of hook-shaped elements secured to the base elements, wherein each of the plurality of hook-shaped elements includes a distal portion connected to a basal portion, wherein the distal portion of each hook-shaped element transitions from a first position that is inclined with respect to the basal portion approximately 90 degrees in a direction toward the longitudinal axis of a respective base element during implantation of the heart valve prosthesis, to a second position in which the distal portion is substantially aligned with respect to the basal portion when the heart valve prosthesis is deployed at a site of implantation for anchoring in a wall of an aorta, wherein the hook-shaped elements extend through the prosthetic valve component prior to the heart valve prosthesis being positioned at the implantation site and are supported inside the prosthetic valve component by a respective base element.

2. An implantable heart valve prosthesis according to claim 1 wherein the plurality of hook-shaped elements are sewn onto the prosthetic valve component.

3. An implantable heart valve prosthesis according to claim 1 wherein each of the plurality of base elements is secured to and aligned with at least one commissure of the prosthetic valve component.

4. An implantable heart valve prosthesis according to claim 3 wherein the at least one commissure of the prosthetic valve component is one of a plurality of commissures, and each of the plurality of base elements is secured to a different commissure of the prosthetic valve component.

5. An implantable heart valve prosthesis according to claim 1 wherein the longitudinal axis of each of the plurality of base elements is substantially aligned with a longitudinal axis of the prosthetic valve component.

6. An implantable heart valve prosthesis according to claim 1 wherein the plurality of base elements are oriented in a helical orientation.

7. An implantable heart valve prosthesis according to claim 1 wherein the hook-shaped elements are made of a shape memory metal.

8. An implantable heart valve prosthesis according to claim 1 wherein the hook-shaped elements are substantially pin-shaped and are provided with barbs.

9. An implantable heart valve prosthesis according to claim 1 wherein the hook-shaped elements include hook portions, the hook portions being bent into various directions.

10. A medical device, comprising:
a heart valve prosthesis;
a first plurality of pin-shaped elements, each securely connected to a first elongated, discrete base element at a respective first end, the first base element attached to the heart valve prosthesis; and
a second plurality of pin-shaped elements, each securely connected to a second elongated, discrete base element at a respective first end, the second base element attached to the heart valve prosthesis;
wherein each of the first and second plurality of pin-shaped elements includes a distal portion and a basal portion, wherein the distal portion of each pin-shaped element transitions from a first position, inclined substantially 90 degrees with respect to the basal portion in a direction toward a longitudinal axis of a respective base element during implantation of the heart valve prosthesis, to a second position, in which the distal portion is substantially aligned with respect to the basal portion when the heart valve prosthesis is deployed at a site of implantation; and
wherein the pin-shaped elements extend through the heart valve prosthesis prior to the heart valve prosthesis being positioned at the implantation site and are supported inside the heart valve prosthesis by a respective base element.

11. The medical device of claim 10, wherein:
the heart valve prosthesis includes at least two commissures;
the first base element is secured to the heart valve prosthesis through a portion of one of the at least two commissures; and
the second base element is secured to the heart valve prosthesis through a portion of another one of the at least two commissures.

12. The medical device of claim 10, wherein the first and second base elements include respective first and second longitudinal axes and each of the first and second longitudinal axes are substantially aligned with a longitudinal axis of the heart valve prosthesis.

13. The medical device of claim 10, wherein the first and second base elements are substantially helically oriented with respect to a longitudinal axis of the heart valve prosthesis.

14. The medical device of claim 10, wherein each of the first and second plurality of pin-shaped elements is made from a shape memory material and is configured to transition from the first position to the second position when a transition temperature of the shape memory material is exceeded.

15. the medical device of claim 10, wherein each of the first and second plurality of pin-shaped elements includes a barb disposed at a respective distal end.

16. A medical device, comprising:
a heart valve prosthesis;
a first plurality of pin-shaped elements, each connected to a first elongated, discrete base element at a respective first end and having a barb disposed at a respective second end, the first base element attached to the heart valve prosthesis; and
a second plurality of pin-shaped elements, each connected to a second elongated, discrete base element at a respective first end and having a barb disposed at a respective second end, the second base element attached to the heart valve prosthesis;
wherein each of the first and second plurality of pin-shaped elements is made from a shape memory material
wherein each of the first and second pluralities of pin-shaped elements includes a distal portion connected to a basal portion, wherein the distal portion of each pin-shaped element transitions from a first position that is inclined with respect to the basal portion approximately 90 degrees in a direction toward a longitudinal axis of a respective base element during implantation of the heart valve prosthesis, to a second position in which the distal portion is substantially aligned with respect to the basal portion when the heart valve prosthesis is deployed at a site of implantation, wherein the pin-shaped elements extend through the heart valve prosthesis prior to the heart valve prosthesis being positioned at the implantation site and are supported inside the heart valve prosthesis by a respective base element.

17. The medical device of claim 16, wherein the first and second base elements include respective first and second longitudinal axes and each of the first and second longitudinal axes is substantially aligned with a longitudinal axis of the heart valve prosthesis.

18. The medical device of claim 16, wherein the first and second base elements include respective first and second longitudinal axes and each of the first and second longitudinal axes are substantially perpendicular to a longitudinal axis of the heart valve prosthesis.

19. The medical device of claim 16, wherein the first and second base elements are substantially helically oriented with respect to a longitudinal axis of the heart valve prosthesis.

* * * * *

UNITED STATES PATENT AND TRADEMARK OFFICE
CERTIFICATE OF CORRECTION

| | | |
|---|---|---|
| PATENT NO. | : 7,896,913 B2 | Page 1 of 1 |
| APPLICATION NO. | : 11/515589 | |
| DATED | : March 1, 2011 | |
| INVENTOR(S) | : Christoph Damm et al. | |

It is certified that error appears in the above-identified patent and that said Letters Patent is hereby corrected as shown below:

Claim 15, col. 6, line 20, "the" should read --The--.

Claim 16, col. 6, line 37, "material" should read --material;--.

Signed and Sealed this

Seventeenth Day of May, 2011

David J. Kappos
*Director of the United States Patent and Trademark Office*